United States Patent [19]
Ansell

[11] Patent Number: 4,914,173
[45] Date of Patent: Apr. 3, 1990

[54] ADHESIVES, THEIR PREPARATION AND USE

[75] Inventor: Christopher W. G. Ansell, Sawston, United Kingdom

[73] Assignee: Smith and Nephew Associate Companies plc, United Kingdom

[21] Appl. No.: 271,096

[22] Filed: Nov. 14, 1988

Related U.S. Application Data

[63] Continuation of Ser. No. 129,526, Dec. 7, 1987, abandoned.

[30] Foreign Application Priority Data

Dec. 6, 1986 [GB] United Kingdom ................. 8629231

[51] Int. Cl.$^4$ ............................................. C08G 18/04
[52] U.S. Cl. ......................................... 528/49; 528/75
[58] Field of Search ................................... 528/49, 75

[56] References Cited

U.S. PATENT DOCUMENTS

| | | | |
|---|---|---|---|
| 4,192,762 | 5/1980 | Osborn | 252/182 |
| 4,465,718 | 8/1984 | Gruber | 528/49 |
| 4,672,001 | 6/1987 | Bravet et al. | 528/75 |

FOREIGN PATENT DOCUMENTS

| | | |
|---|---|---|
| 0094222 | 11/1983 | European Pat. Off. |
| 0175474 | 3/1986 | European Pat. Off. |
| 1242622 | 8/1971 | United Kingdom |
| 1430422 | 3/1976 | United Kingdom |
| 1441108 | 6/1976 | United Kingdom |
| 1489163 | 10/1977 | United Kingdom |
| 1509447 | 5/1978 | United Kingdom |
| 1545061 | 5/1979 | United Kingdom |
| 2030991 | 4/1980 | United Kingdom |
| 2086927 | 5/1982 | United Kingdom |
| 2131442 | 6/1984 | United Kingdom |
| 2150938 | 7/1985 | United Kingdom |

OTHER PUBLICATIONS

Chemical Abstract 92999q—abstract of Japanese Patent 734 7538.

Primary Examiner—Maurice J. Welsh
Attorney, Agent, or Firm—Jacobs & Jacobs

[57] ABSTRACT

Skin friendly pressure sensitive adhesives in the form of inherently tacky polyurethane-containing gells may be prepared by reacting an isocyanate prepolymer, which is itself the reaction product of poly-functional isocyanate and polyoxyalkylene diol monoalkyl ether, with a hydroxyl-containing ester of acrylic or methacrylic acid and optionally other hydroxyl containing compounds and then cross-linking the polymer so formed by means of irradiation. The proportion of acrylate chosen is such that it will react with at least 15 to 25% of the free isocyanate groups in the prepolymer and the remainder react with the other hydroxyl containing compound. The adhesives are capable of absorbing up to 95%, typically from 35 to 95% by weight of water when hydrated. The use of the adhesive in highly moisture vapor permeable dressings is also disclosed.

15 Claims, No Drawings

ADHESIVES, THEIR PREPARATION AND USE

This is a continuation of Ser. No. 129,526, filed Dec. 7, 1987, now abandoned.

The present invention relates to an adhesive which is suitable for use on skin and which comprises polyurethane polymer which is capable of absorbing water.

Conventionally adhesives employed for skin contact have comprised synthetic polymer adhesives such as polyacrylates or polyvinyl alkyl ethers. Disadvantages associated with the use of this type of adhesive are known. Polyacrylate adhesives may, for example, occasionally cause skin irritation and maceration a condition which may be worsened if the adhesive is left in contact with the skin for long periods, as for example, when used on so-called intravenous dressings for covering cannula sites and the like. A further disadvantage which may arise with thin film dressings is that although the adhesives employed are moisture vapour permeable, the moisture vapour permeability of the adhesive when present as a continuous film is not sufficiently high to permit rapid evaporation of moisture from a dressing which has been applied to an exuding wound, i.e., when the adhesive is in contact with an aqueous fluid. Furthermore, these adhesives are not absorbent to water and indeed may be deleteriously affected by water. The result of using such an adhesive can be to cause the formation of an unsightly blister which can predispose to leakage and so lead to bacterial contamination.

It would be an advantageous therefore if an adhesive could be found possessing a high moisture vapour permeability so that it could be present as a continuous layer on a dressing for use on an exuding wound and also one which had little propensity to cause irritation even after prolonged contact with the skin and could also be used, for example, on an intravenous dressing or incise drape.

We have now found an adhesive comprising water absorbent polyurethane-containing polymer which is suitable for use on the skin. When used in combination with a suitable backing layer for example a moisture vapour permeable, continuous, conformable polymeric film, various types of bacteria-proof adhesive dressing maybe provided which are conformable to the body surface, absorb exudate when used on exuding wounds while preventing dehydration of the wound, even when exudation has ceased, so providing a moist environment for improved wound healing, permit inspection of the healing wound, protect the wound from mechanical trauma and can serve as a carrier for topically applied pharmacologically active agents or medicaments such as antibacterials and antimicrobials and can remain on intact skin for long periods of time without deleterious effects. It is particularly surprising that the adhesive properties of the polyurethane are not unduly affected by wound exudate and are satisfactorily maintained when the polyurethane is both 'wet' and 'dry'. The dressings may remain in place over a wound for a period of days yet the dressings maybe removed without causing discomfort or compromising the healing wound. It has also been found that even on non-exuding wounds, the environment at or near the wound is maintained in a moist condition which is conducive to wound healing.

United Kingdom Pat. No. 2094809 and U.S. Pat. No. 4505976 describe a pressure sensitive adhesive composition which has the capacity to absorb from about 15% to 40% its own weight of water. However, the pressure sensitive adhesive per se is not water absorbent. The adhesive contains an additional component which is water absorbent. This is also true of the adhesives described in United Kingdom Pat. No. 2008000B.

Accordingly the present invention provides a skin friendly pressure sensitive adhesive which comprises an inherently tacky polyurethane gel which adhesive contain both polyurethane and acrylate residues and which is nots self-adherent.

The polyurethane component of the adhesives of the invention absorbs water e.g., from 5 to 95% of the weight of the adhesive to form a gel, but retains its adhesiveness. While in the form of a gel the adhesive retains its integrity and does not delaminate from its substrate.

The adhesives of the invention also have the advantage that they are non-self-adherent so that if for example the adhesive surface becomes creased during the application of a dressing the contacting surfaces of the adhesive may be easily peeled apart and the dressing is not wasted.

The gel may be in the form of a layer, film and may contain bubbles and could even have the appearance of a foam because of such bubbles. However, the gel is most aptly provided in the form of a bubble-free layer such as a thin film or a thick layer.

The adhesive may be prepared as a wet or dry adhesive. A 'wet' adhesive contains water that is it may be prepared in the presence of an excess of water. A 'dry' adhesive is one prepared in the absence of water or which may be formed by allowing water to evaporate from a wet adhesive. Such 'dry' adhesives may have a water content of less than 5%.

By water absorbent is meant that the polyurethane will absorb water and become hydrated and when hydrated may contain up to 95%, typically from 35 to 95% by weight of water aptly 50 to 92%, preferably 70 to 90% by weight of water and most preferably 75 to 85% by weight of water.

The water absorption of the adhesive can be obtained by taking a known weight of the dry adhesive (D) and immersing in water for 24 hours. The hydrated polymer is removed from the water, surface water is removed by lightly blotting with absorbent paper and then the weight of the hydrated adhesive (W) taken. The water absorption of the adhesive (% by weight) can then be calculated as $(W-D) \times 100/W$.

The polyurethane adhesive may be prepared by reacting isocyanate prepolymer, which itself can be the reaction product of polyfunctional isocyanate and polyoxyalkylene diol monoalkyl ether, with an acrylate comprising hydroxyl-containing ester of acrylic or methacrylic acid and optionally other hydroxyl containing compounds such as water or one or more polyols whereby the proportion of the acrylate is desirably such that it will react with at least from 15 to 25% of the free isocyanate groups in the prepolymer. Any other hydroxyl -containing compounds present will react with the remainder of the isocycnate groups. Polymer formed may be cross-linked for example by irradiation.

The other hydroxyl containing compounds may be monools or polyols such as diols or triols such as primary alcohols but preferably they are polyoxyalkylene diol monoalkyl ethers as hereinafter defined or other monools which may confer additional tacky properties to the adhesive. Such monools include hydrogenated mono hydroxylin tackifying resins such as hydrogenated abietyl alcohol.

Suitable polyoxyalkylene diol mono alkyl ethers for use in forming the prepolymers and polymers employed to prepare the adhesives of the present invention include those in which the alkyl group contains from 1 to 18 carbon atoms and more suitably 2 to 6 carbon atoms and preferably 2 to 12 carbon atoms for example 4 carbon atoms that is the mono alkyl ether is a monobutyl ether.

Suitably the polyoxyalkylene residue in the mono alkyl ether is a hydrophilic residue that contains polyoxyethylene or polyoxypropylene residues or mixtures thereof. Preferred polyoxyalkylene residues are those which contain a mixture of polyoxyethylene and polyoxypropylene residues in a ratio of from 20:80 to 80:20 for example 50:50 and in which residues are random randomly arranged with respect to each other.

A preferred polyoxyalkylene diol mono alkyl ether is therefore polyoxyethylene-polyoxypropylene mono butyl ether in which the ratio of polyoxyethylene to polyoxypropylene residues is 50:50 such as Entarox polyols available from ICI.

Aptly the molecular weight of the monoalkyl ether is from 3000 to 12000, and more suitably is 4000 to 10000 and preferably is 5000 to 9000. It has been found that polyoxyalkylene diol monoalkyl ethers within this molecular weight range provide polymers which are tacky and suitable for use on the skin while use of lower molecular weight materials tend to provide polymers which are not suitable for use as adhesives because they are insufficiently tacky.

The polyoxyalkylene diol mono alkyl ethers for use in forming the prepolymer or polymer will normally contain water. It is preferred however that the polyoxyalkylene diol monoalkyl ether contains less than 1% by weight of water so as to limit the proportion of urea groups formed in the reaction with the polyisocyanate.

The polyisocyanate used for forming the prepolymer will have a functionality of greater than 2 and may suitably have a functionality of from 2.1 to 5 and more suitably from 2.2 to 3.5 and preferably from 2.5 to 3.0 for example 2.5, 2.7, 2.85 or 2.9. Suitable polyisocyanates include (cyclo) aliphatic and aromatic polyisocyanates- Preferred polyisocyanates are aromatic polyisocyanates for example those based on a polymeric methylene di phenyl diisocyanate, for example the Suprasecs (trade mark), which are available from I.C.I. It is preferred that the functionality of the isocyanate is not more than 3 as this leads to a higher cross-link density and is manifest ultimately as a harder adhesive which may not be advantageous for an adhesive which is to be applied to the skin.

The prepolymers may be simply prepared by heating the two components together in the required proportions at an elevated temperature for sufficient time for the reaction to be completed, for example 90° C. for 2 hours, in the presence of a conventional polyurethane polymerisation catalyst such as 0.2% w/w catalyst of dibutyl tin dilaurate (T12). The mole ratio NCO/OH is suitably from 2.0 to 4.0 in this reaction and the prepolymer so formed contains fom 1.5 to 3.0% by weight of free-isocyanate groups.

The adhesives of the present invention may be prepared by reacting the isocyanate prepolymer described above with hydroxy-containing compounds a proportion of which also contains an unsaturated functionality which is reactive when exposed to irradiation for example ultra violet or electron beam irradiation.

Suitable unsaturated compounds include esters of acrylic or methacrylic acid in which there is at least one hydroxyl functional group which is capable of reacting with isocyanate present. Preferred esters include hydroxy ethyl methacrylate and methacrylate mono-esters of of polyoxylalkylene diols in which the number of repeating ether units is from 1 to 25 and preferably 2 to 10, for example 6.

After reaction between the isocyanate prepolymer and the hydroxyl-containing compounds the resulting polymer has therefore pendant unsaturated groups which are capable of interacting with each other to cross-link the polymer under the influence of a polymerisation initiator and irradiation. One suitable form of radiation is ultraviolet irradiation. The polymer may be mixed with a photoinitiator and the mixture irradiated by means of ultraviolet radiation. This causes the polymer to become cross-linked.

The polyurethane polymer so formed is a cross-linked polymer which is capable of absorbing from 5 to 95% by weight of water depending upon the reactants employed.

Alternatively the adhesive may be formed as a 'wet' adhesive by dispersing the uncross-linked polymer and photoinitiator in an appropriate volume of water and then irradiating to form the adhesive. Suitably the wet adhesive may contain from 40 to 65% by weight of water.

In another aspect the present invention also provides a process for the preparation of skin friendly pressure sensitive adhesive in the form of an inherently tacky polyurethane-containing gel, typically containing from 5 to 95% by weight of water when hydrated which process comprises reacting an isocyanate prepolymer, which is itself the reaction product of polyfunctional isocyanate and polyoxyalkylene diol monoalkyl ether, with an acrylate comprising a hydroxyl-containing ester of acrylic or methacrylic acid and polyol in which the proportion of the acrylate is such that the hydroxyl groups contained therein will react with from 15 to 25% of the free isocyanate groups in the prepolymer and cross-linking the polymer formed by means of irradiation.

In a further aspect, the present invention provides adhesive products comprising adhesives in accordance with the invention.

The adhesives of the present invention are suitable for use in a number of applications. These applications include use as the adhesive when coated on a substrate for bandages, absorbent dressings, wound dressings, burns dressings, incise drapes, first aid dressings, intravenous catheter dressings, ulcer dressings, ostomy devices, condom attachment in urinary incontinence devices, transdermal drug delivery devices, electroconductive gels, adhesive tapes (surgical tapes, wound closure tapes and the like), sanitary protection devices such as napkins, diapers, incontinence pads and protection pads against physical trauma or vibrations. However the main use is envisaged to be in dressings and drapes of the types described above when the adhesive is in contact with the skin.

The adhesives of the invention may be employed in the manufacture of bacteria proof wound dressings such as those which comprise a backing layer which has upon substantially the whole of one surface thereof a layer of pressure sensitive adhesive in accordance with the invention. Such dressings will typically have a moisture vapour transmission rate of greater than 7000 $gm^{-2} 24h^{-1}$ at 37° C. when the adhesive is in contact with water.

Suitably the adhesive layer may be microscopically continuous over the whole of the surface of the backing layer.

Many medicinal agents may be incorporated into the adhesives of the present invention. By medicinal agents it is meant pharmacologically active agents and agents including topical anaesthetics such as xylocaine, bacteriostatic agents such as silver nitrate; antibacterial agents of which preferred agents are silver sulphadiazine, chlorhexidine salts, PVP-I, and biguanides antibiotics; topical steroids, enzymes, tissue stimulants, coagulants and anticoagulants and antifungal agents. Other agents such as emollients may be added after the reaction step.

Advantageously water soluble medicaments such as chlorhexidine and its salts may be dissolved in the water which is used to react with the prepolymer. It is found that chlorhexidine is unaffected during the process and the resulting adhesive provides effective release of chlorhexidine when placed onto the skin.

A suitable method of determining the upright moisture vapour transmission rate of the dressing of this invention is as follows. Discs of material under test are clamped over Payne Permeability Cups (flanged metal cups) using sealing rings and screw clamps. The exposed surface area of the test sample may be conveniently 10 cm². Each cup contains approximately 10 ml of distilled water. After weighing the cups are placed in a fan assisted electric oven maintained at 37±1° C. The relative humidity within the oven is maintained at 10% by placing 1 Kg of anyhdrous 3–8 mesh calcium chloride on the floor of the oven. The cups are removed after 24 hours, allowed to cool for 20 minutes and re-weighed. The MVTR of the test material is calculated from the weight loss expressed in units of grams of weight per square meter per 24 hours.

A suitable method of determining the inverted moisture vapour transmission rate of the dressing of this invention is as follows. The method described above is employed except that the Payne Cups are inverted in the oven so that the water within the cups is in contact with the test material and in this case with the adhesive.

EXAMPLE 1

A polyoxyethylene - polyoxypropylene diol monobutyl ether (87.4 g, 0.026 moles based on OH value) and a polymeric methylene diphenylene diisocyanate (12.6 g, oaving an isocyanate functionality of 2.5 the NCO-/OH=2.5) were mixed together in a 700 cc flange flask fitted with an overhead stirrer and immersed in a water bath at 90° C. A catalyst of dibutyl tin dilaurate (0.2% w/w) was added. The mixture was stirred at 90° C. for about 2 hours. The isocyanate content of the prepolymer so formed was 1.98%. Sufficient of 2-hydroxyethyl methacrylate to react with 20% of the available isocyanate groups was added together with an acrylic polymerisation inhibitor (methoxyethyl hydroquinone) (500 ppm) and then sufficient of the polyoxyethylene -polyoxypropylene diol monobutyl ether was added to react with the remaining isocyanate groups. The temperature of the mixture was reduced to 60° C. and the mixture was stirred for about 1 hour. The final product was isolated as a golden yellow viscous liquid.

A photoinitiator, benzildimethyl ketal (1% w/w) was dispersed in the polymer and the mixture spread as a layer 2 mm thick between two polytetrafluoroethylene sheets and irradiated with ultraviolet radiation typically between 219 and 425 nm. The cross-linked polymer so formed had adhesive properties and absorbed 82% by weight of water when fully hydrated.

A thin film of this adhesive as a microscopically continuous layer at a weight per unit area of 70 $gm^{-2}$ on a backing layer of a hydrophilic polyurethane for which polyurethane contains 25% by weight of water when hydrated, at a weight per unit area of 42 $gm^{-2}$ provided an bacteria proof dressing which has an upright moisture vapour transmission rate of 1400 $gm^{-2}24h^{-1}$ at 37° C. and 100% to 10% relative humidity difference and an inverted moisture vapour transmission rate of 10500 $gm^{-2}24h^{-1}$ at 37° C.

EXAMPLES 2–4

Adhesives were prepared in a similar manner to Example 1 except that the acrylate used was polypropyleneglycol methacrylate (PPGMM).

| Example | % of NCO groups neutralised by PPGMM | Neutralising agent for remainder of NCO | Water absorbency (% by weight) |
|---------|--------------------------------------|------------------------------------------|-------------------------------|
| 2 | 25 | n-butanol | 81.6 |
| 3 | 20 | 1-decanol | 78.0 |
| 4 | 20 | polyoxyethylene-polyoxypropylene diol mono buthyl ether | 84.0 |

EXAMPLE 5

An adhesive was prepared in a similar manner to Example 1 except that the neutralising agent for the remainder of the isocyanate groups in the prepolymer was hydrogenated abietyl alcohol. The adhesive as formed has a water absorbency of 85%.

What is claimed:

1. A skin friendly pressure sensitive adhesive suitable for use on skin which comprises an inherently tacky polyurethane gel which adhesive contains both polyurethane and acrylate residues and which is not self-adherent, and which contains up to 95% by weight of water when hydrated.

2. An adhesive according to claim 1 in which the adhesive contains from 35 to 95% by weight of water when hydrated.

3. As adhesive according to claim 1 in which the adhesive is a cross-linked reaction product of an isocyanate prepolymer, which is itself the reaction product of polyfunctional isocyanate and polyoxylalkylene diol monoalkylether, with an acrylate comprising hydroxyl-containing ester of acrylic or methacrylic acid and at least one other hydroxyl containing compound whereby the proportion of the acrylate is such that it reacts with from 15 to 25% of the free isocyanate groups in the prepolymer, the other hydroxyl - containing compound reacting with the remainder.

4. An adhesive according to claim 3 in which the acrylate is selected from the group consisting of hydroxyethyl methacrylate and methacrylate-mono-esters of polyoxyalkylene diols in which the number of repeating ether units is from 1 to 25.

5. An adhesive according to claim 3 in which in the polyoxyalkylene diol monoalkyl ether the alkyl group contains from 2 to 6 carbon atoms and the polyoxyalkylene comprises a mixture of polyoxyethylene and polyoxypropylene in a ratio of from 20:80 to 80:20.

6. An adhesive according to claim 2 in which the polyisocyanate has a functionality of from 2.2 to 3.5.

7. An adhesive according to claim 3 in which the said other hydroxyl containing compound is polyoxyalkylene diol monoalkyl ether.

8. An adhesive according to claim 3 in which the said other hydroxyl containing compound is a tackifying resin.

9. An adhesive according to claim 8 in which the tackifying resin is hydrogenated abietyl alcohol.

10. An adhesive according to claim 1 having an effective amount of a medicinal agent incorporated herein.

11. A process for the preparation of a skin friendly pressure sensitive adhesive in the form of an inherently tacky polyurethane gel which process comprises reacting an isocyanate prepolymer, which is itself the reaction product of polyfunctional isocyanate and polyoxyalkylene diol monoalkyl ether, with acrylate comprising a hydroxyl-containing ester of acrylic or methacrylic acid in which the proportion of the acrylate is such that the hydroxyl groups contained therein will react with from 15 to 25% of the free isocyanate groups in the prepolymer and cross-linking the polymer formed by means of irradiation.

12. A process according to claim 11 in which at least one other hydroxyl-containing compound is also present to react with the remaining free isocyanate group.

13. A process according to claim 12 in which the other hydroxyl-containing compound is polyoxyalkylene diol monoalkyl ether.

14. A process according to claim 12 in which the other hydroxyl-containing compound is hydrogenated abietyl alcohol.

15. An adhesive product comprising a substrate which contains on one surface thereof an adhesive according to claim 1.

* * * * *